United States Patent [19]
Mandralis et al.

[11] Patent Number: 6,048,562
[45] Date of Patent: Apr. 11, 2000

[54] ENCAPSULATION PROCESS

[75] Inventors: Zenon Ioannis Mandralis, Dublin, Ohio; James Tuot, Newtown, Conn.

[73] Assignee: Nestec S.A., Vevey, Switzerland

[21] Appl. No.: 08/673,227

[22] Filed: Jun. 28, 1996

[51] Int. Cl.[7] ............................... A23L 1/22; A23L 1/226
[52] U.S. Cl. ............................ 426/573; 426/96; 426/97; 426/98; 426/638; 426/650; 426/651; 264/4.1; 264/4.7
[58] Field of Search ................................. 426/96, 98, 573, 426/97, 138, 72, 285, 297, 311, 638, 650, 651; 264/4.1, 4.3, 4.7; 427/213.3, 213.34, 213.35, 2; 428/402.21

[56] References Cited

U.S. PATENT DOCUMENTS

| | | | |
|---|---|---|---|
| 3,860,733 | 1/1975 | Morse et al. | 426/96 |
| 3,870,812 | 3/1975 | Hayes, Jr. et al. | 426/573 |
| 3,962,416 | 6/1976 | Katzen | 426/96 |
| 4,217,370 | 8/1980 | Rawlings et al. | 426/98 |
| 4,230,687 | 10/1980 | Sair et al. | 426/96 |
| 4,232,047 | 11/1980 | Sair et al. | 426/96 |
| 4,276,312 | 6/1981 | Merritt | 426/96 |
| 4,386,106 | 5/1983 | Merritt et al. | 426/5 |
| 4,515,769 | 5/1985 | Merritt et al. | 426/96 |
| 4,582,719 | 4/1986 | Kaetsu et al. | 427/2 |
| 4,634,598 | 1/1987 | Liu et al. | 426/650 |
| 4,814,274 | 3/1989 | Shioya et al. | 435/174 |
| 5,021,248 | 6/1991 | Stark et al. | 426/96 |
| 5,164,126 | 11/1992 | Kalishek et al. | 264/4.7 |
| 5,173,321 | 12/1992 | Hosogoe et al. | 426/96 |
| 5,204,029 | 4/1993 | Morgan et al. | 426/96 |
| 5,266,335 | 11/1993 | Cherukuri et al. | 426/96 |
| 5,271,881 | 12/1993 | Redding, Jr. | 264/432 |
| 5,418,010 | 5/1995 | Janda et al. | 426/96 |
| 5,441,878 | 8/1995 | Thies et al. | 435/178 |
| 5,478,508 | 12/1995 | Suzuki et al. | 426/96 |
| 5,498,439 | 3/1996 | Bonner | 426/574 |
| 5,536,513 | 7/1996 | Graf et al. | 426/573 |
| 5,549,917 | 8/1996 | Cherukuri et al. | 426/96 |
| 5,585,051 | 12/1996 | Hosie et al. | 264/4.1 |
| 5,601,760 | 2/1997 | Rosenberg | 264/4.1 |
| 5,932,272 | 8/1999 | Raemy et al. | 426/573 |

OTHER PUBLICATIONS

High Pressure and Biotechnology, Eds C. Balny et al. Colloque INSERM/John Libbey Eurotext ltd. 1992, vol. 224, pp. 89–99 "Pressure denaturation of proteins", by Patrick Masson.

High Pressure and Biotechnology, Eds C. Balny et al. Colloque INSERM/John Libbey Eurotext ltd. 1992, vol. 224, pp. 105–113 by Kunihiko Gekko.

High Pressure and Biotechnology, Eds C. Balny et al. Colloque INSERM/John Libbey Eurotext ltd. 1992, vol. 224, pp. 185–193 "Utilization of pressure in addition to temperature in food science technology" by Rikimaru Hayashi.

High Pressure and Biotechnology, Eds C. Balny et al. Colloque INSERM/John Libbey Eurotext ltd. 1992, vol. 224, pp. 195–209 "effects of high hydrostatic pressure on food constituents: an overview" by Jean–Claude Cheftel.

High Pressure and Biotechnology, Eds C. Balny et al. Colloque INSERM/John Libbey Eurotext ltd. 1992, vol. 224, pp. 509–514, "High pressure equipment for food processing" by A. Traff et al.

High Pressure and Biotechnology, Eds C. Balny et al. Colloque INSERM/John Libbey Eurotext ltd. 1992, vol. 224, pp. 515–519, "Packaging for high pressure food processing" by Shinya Ochiai et al.

Journal of Controlled Release, 14 (1990) 111–131, Elsevier Science Publishers B.V., Amsterdam "Albumin Microspheres and Microcapsules: Methodology of Manufacturing Techniques" by R. Arshady.

J. Microencapsulation, 1989, vol. 6, No. 4, 427–462, "Albumin microspheres I: physico–chemical characteristics" By P.K. Gupta et al.

J. Microencapsulation, 1989, vol. 6, No. 4, 463–472, "Albumin microspheres II: applications in drug delivery" by P.K. Gupta et al.

*Primary Examiner*—Cynthia L. Nessler
*Attorney, Agent, or Firm*—Pennie & Edmonds LLP

[57] ABSTRACT

A process for encapsulating a core material by mixing the core material with an aqueous medium comprising a natural polymer and treating the formed mixture at a pressure of from about 15,000 to 200,000 psi at a temperature of from about 0° to 100° C. to form a gel matrix comprising the core material encapsulated within the natural food polymer and then drying the resulting product.

20 Claims, 3 Drawing Sheets

ENCAPSULATION PROCESS

FIELD OF THE INVENTION

The present invention relates to an encapsulation process, more particularly to a process for encapsulating a core material with a natural polymer.

BACKGROUND OF THE INVENTION

In the food industry, encapsulation may be used to stabilize the core material, and to control the timing and rate of the release of the core material. Thus, encapsulation makes it possible to protect sensitive food components, to ensure against nutritional loss and to mask or preserve flavors and aromas. Encapsulation also increases the stability of vitamin or mineral supplements, for example, which are normally sensitive to UV radiation, light, oxygen, metals, humidity and temperature. Moreover, encapsulation is also utilized in the pharmaceutical industry to protect the lining of the mouth and oesophagus from harsh orally administered drugs which are released in the stomach by the action of stomach acids and enzymes on the capsule coating, or for controlled release of drugs delivered through intramuscular, subcutaneous or intravenous routes.

Proteins (whey, soy, gelatin, egg albumin, casein, human serum albumin etc.) and polysaccharides (starch, carboxymethyl cellulose etc.) have been used as wall materials for the encapsulation of various ingredients. A review of the techniques used is given by Gupta, P. K. and Hung, C. T., "Albumin Microspheres: applications in drug delivery," J.Microencapsulation, (1989), 6, 464–472 and R.Arschady, "Albumin Microspheres and Microcapsules: Methodology of manufacturing techniques," Journal of Controlled Release, 14 (1990) 111–131. Typically, the active ingredient is dissolved, emulsified or dispersed in a solution of protein in water and then the protein is denatured and becomes water insoluble, thus entrapping the active ingredient. Depending on the desired capsule shape and size, various techniques are also described in the literature ranging from simple grinding to forming double emulsions in oil media prior to denaturation. However, it is common in all techniques that the denaturation process is performed either by heat (100–180° C.) or by chemical crosslinking with suitable crosslinking agents such as glutaraldehyde. It is clear that heat denaturation is not suitable in the case of heat sensitive active ingredients such as some vitamins, aromas, flavors or drugs such as methotrexate, epinephrine, salbumatol is discussed by Gupta and Hung "Albumin Microspheres: Physicochemical characteristics," J.Microencapsulation, (1989), 6 427–461. Chemical crosslinking is also not suitable when the use of chemicals is not approved by food or drug regulations.

SUMMARY OF THE INVENTION

We have devised an encapsulation process whereby the above disadvantages of the use of heat and chemicals can be overcome by using a natural polymer as encapsulating material and treating a mixture of the core material and the encapsulating material at high pressure and at a temperature from about 0° C. to 100° C.

According to the present invention, there is provided a process for encapsulating a core material which comprises mixing the core material with an aqueous medium comprising a natural food polymer and treating the formed mixture at a pressure of from 15,000 to 200,000 psi and at a temperature of from 0° to 100° C. to form a gel matrix comprising the core material encapsulated within the natural polymer and then drying the resulting product.

DETAILED DESCRIPTION OF THE INVENTION

Figure 1:
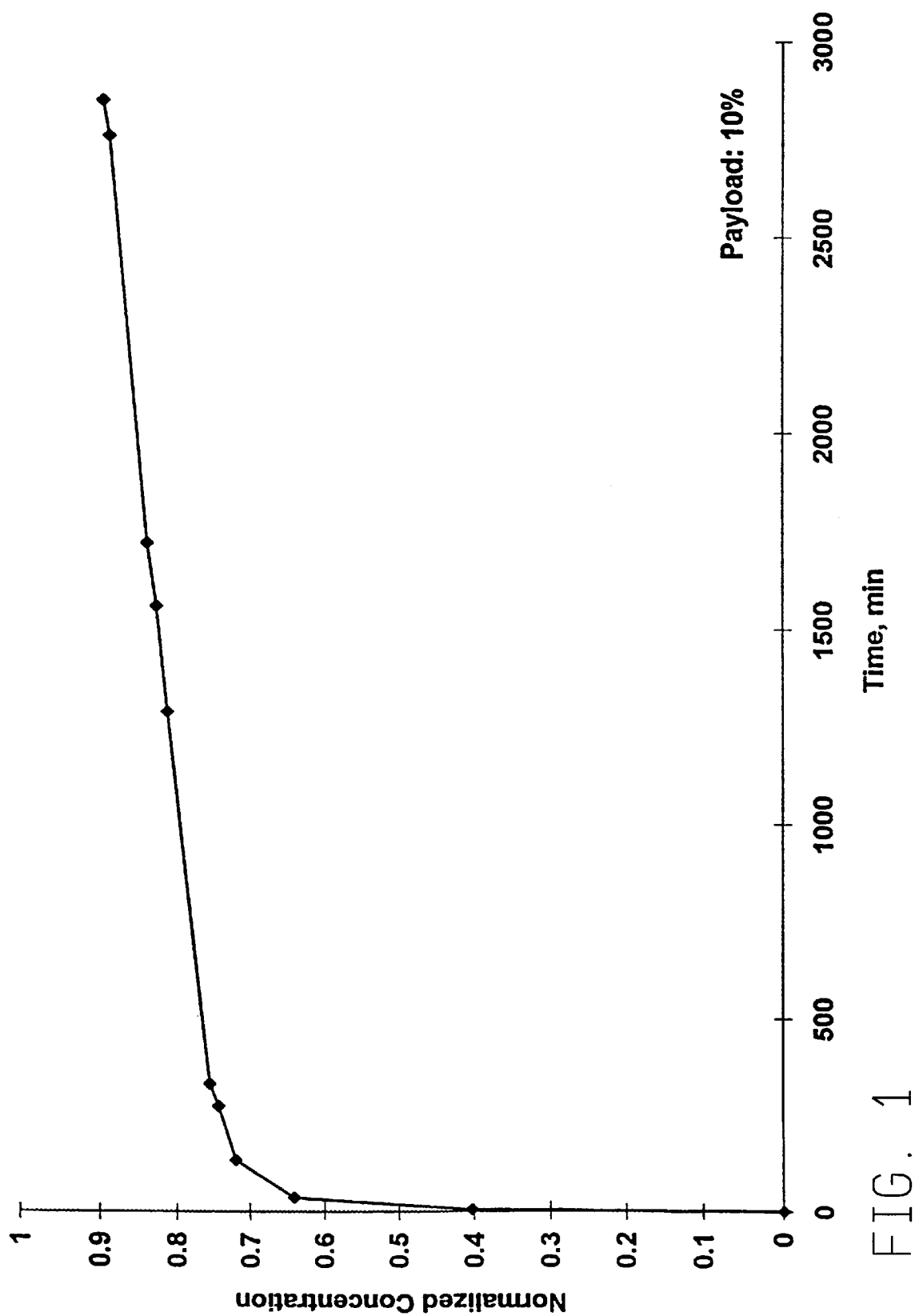
FIG. 1 is a graph illustrating release of the core material over time.

If desired, before the pressure treatment, the process comprises mixing the formed mixture with melted fat to form a water in oil emulsion containing droplets, cooling the emulsion to solidify the fat phase, then pressure treating the emulsion to transform the droplets into gel particles, separating the gel particles from the fat phase and washing the separated gel particles.

The capsules formed may be microcapsules having a particle size of from 1 micron to 3 mm, preferably from 2 microns to 2 mm and more preferably from 5 microns to 0.5 mm. The core material may be solid or liquid and may be a substance used in the food industry such as a flavor, color, vitamin, mineral, spice or oil, or it may be a pharmaceutical. The present invention is particularly advantageous when the core material is heat sensitive or chemically sensitive.

The polymer encapsulating material may be a polysaccharide such as pectin or a gum, e.g. carboxymethyl cellulose, low methoxy pectin, alginate, starch, etc. or it may be any protein whether of animal or vegetable origin and which is water-soluble or water-dispersible, e.g. whey protein, casein, gelatin, human serum albumin, egg white or soy isolate. The polymer encapsulating material should preferably be non-toxic, water-insoluble after the high pressure treatment, biocompatible and biodegradable, a good barrier against oxygen and diffusion losses, and approved by regulatory bodies for use in food or pharmaceutical products.

A detailed review of the behaviour of various macromolecules under high pressure treatment is given in "High Pressure and Biotechnology", Eds C.Balny, R.Hayashi, K.Heremans & P.Masson, Colloque INSERM/John Libey Eurotext Ltd., 1992. Vol 224, pp. 89, 105, 185, 195.

The core material may conveniently be mixed with the aqueous polymer medium by either dissolving, emulsifying or dispersing it into an aqueous solution, dispersion or slurry of the polymer. The temperature of the high pressure treatment is preferably from about 15° C. to 60° C., more preferably from about 20° C. to 40° C. and suitably at ambient temperature. The pressure is preferably from about 40,000 to 150,000 psi and more preferably from about 60,000 to 120,000 psi. The high pressure treatment may be carried out in a vessel which can withstand the high pressures involved, preferably a hydrostatic press using for instance, water and/or oil as the liquid medium. Before being placed in the vessel, the mixture of the core material with the polymer may be sealed in a flexible bag made of rubber or a plastics material which may be made of any food-acceptable flexible plastics material, e.g. PVC. A review of available high pressure equipment and the types of flexible bags that can be used with high pressure treatment is given by "High Pressure and Biotechnology," Eds C. Balny, R. Hayashi, K. Heremans & P. Masson, Colloque INSERM/John Libey Eurotext Ltd., 1992. Vol. 224, pp. 509, 515. The duration of the high pressure treatment should be sufficient to form a gel, e.g. at least 30 seconds, preferably from about 1 to 60 minutes and more preferably from about 5 to 45 minutes. Periods of time longer than 60 minutes may be used but there is no advantage in doing so. The pH during the high pressure treatment may be from 2 to 8 but is advantageously from 4 to 7 and, when the polymer is a protein, is usually the natural pH of the protein.

In one encapsulation method, after the high pressure treatment, the gel matrix containing the dissolved, emulsified or dispersed active ingredients is first ground to the desired particle size and then dried by any known methods such as vacuum drying, chemical dehydration, freeze drying, convection oven drying, absorptive drying, etc. Alternatively, the gel the matrix is dried first and then ground to the desired particle size.

If it is desired that spherical microcapsules are formed, an alternative procedure can be followed. The solution, emulsion or dispersion of the core material in the water/polymer system is added to a fat phase which is kept at a temperature slightly higher than the melting of the fat point (typically 30–60° C.). By stirring, an emulsion is formed of the desired droplet size. Any suitable surfactant can be added in this phase to form a stable emulsion. Then, the system is sealed in the flexible bag and is cooled rapidly so that the fat phase solidifies before the emulsion droplets are allowed to coalesce. The bag is then treated at high pressure. After high pressure application for the desired time, the immobilized droplets within the fat phase will form a gel phase because of protein denaturation and a spherical shell will form that surrounds the core. By raising the temperature of the system above the fat melting point, the spherical capsules can be separated from the fat phase (by any known technique such as filtration, centrifugation, decantation, etc.). Any food-acceptable oil or fat may be used, e.g. cocoa butter, corn oil, safflower oil, olive oil, hydrogenated soybean oil or any other hydrogenated vegetable oil. It is desired to have the fat solidified during the high pressure treatment so that the microcapsules do not coalesce and this may be achieved with any oil if the resulting emulsion is stable throughout the duration of the treatment. Suitable lipophilic emulsifiers to prepare water in oil emulsions are glyceryl monooleate, propylene glycol monostearate, glyceryl monostearate, lecithin and sorbitan monostearate, etc.

The amount of core material in the mixture with the aqueous polymer medium may be from 0.5 to 30%, preferably from 1 to 10% and more preferably from 2 to 8% by weight based on the total weight of the mixture. The amount of polymer in the aqueous polymer medium may be from 1 to 50% and preferably from about 5 to 30% by weight based on the total weight of the aqueous polymer medium.

If desired, preservatives such as sodium citrate or sodium bisulphite may be added to the mixture of the core material with the aqueous polymer to prevent oxidation of the core material.

EXAMPLES

The present invention will now be further illustrated with reference to the following examples in which parts and percentages are given by weight.

Example 1

1 part of egg albumin was mixed with 0.1 part of FD&C Blue # 1 dye and dissolved in 3 parts of water. The solution was added to 200 parts of Malaysian cocoa butter containing 0.1 part of Tween 80 as emulsifier and stirred continuously at 300 rpm at a temperature of 35° C. The emulsion was than placed in a flexible PVC pouch. It was then immediately cooled in order to solidify the cocoa butter phase and prevent coalescence of the droplets. The flexible pouch was placed in a Quintus QFP-6 High Pressure Processor supplied by ABB Autoclave Systems, Inc. and pressurized to 128,000 psi for 40 min. During pressurization the temperature increased from 16° C. to 42° C. The capsules formed were filtered from the fat phase and washed from surface fat with ethyl ether. The blue dye release from the capsules was tested by adding 0.05 parts of the capsules in 1000 parts of room temperature water under continuous stirring. A Spectronic 21D absorption meter was calibrated against standards of blue dye of known concentration and used to measure the release of the dye vs. time. FIG. 1 shows that a fast release of dye (probably surface dye) was followed by a much slower release. Approximately 50% released during the first 8 hours and only 55% had released after 2 days.

Comparative Example A

Figure 2:
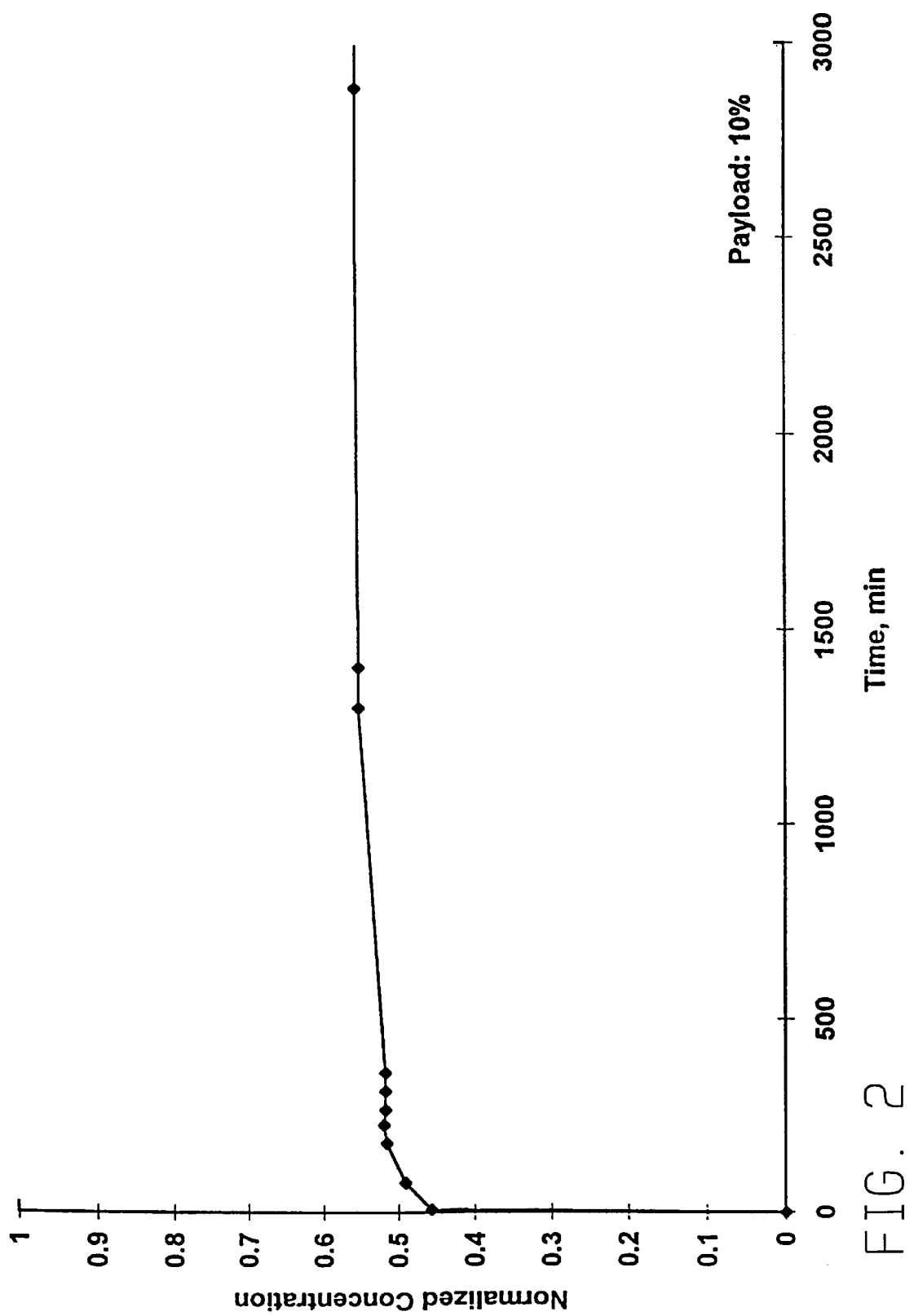
FIG. 2 is a graph of comparative results illustrating release of the core material over time.

By following an essentially similar procedure to that described in Example 1 but using corn oil instead of the Malaysian cocoa butter, and excluding the high pressure treatment in the flexible pouch, as shown in FIG. 2 approximately 70% of the dye (probably surface dye) released from the capsules after 8 hours and 90% had released after 2 days. This indicates poorer encapsulation when compared with the capsules of Example 1 in which the emulsion had undergone a high pressure treatment.

Example 2

25 parts of whey protein (Bi-Pro, 95%, Bio-Isolates Ltd) were dissolved in 100 parts of water and 0.06 parts of a micronutrient vitamin premix was added. The experiment was conducted at pH 5 and 7. The solution was placed in a flexible pouch and pressurized at room temperature at 60,000 psi for 20 min. The resulting gel matrix was ground and vacuum dried. Analysis of the vitamin content of the dried particles indicated that all vitamin E and vitamin B1 contained therein survived the high pressure treatment at both pH levels. The texture of the denatured protein at pH 7 is more elastic, glossy and transparent than that of pH 5 which is more brittle and opaque.

Example 3

Figure 3:
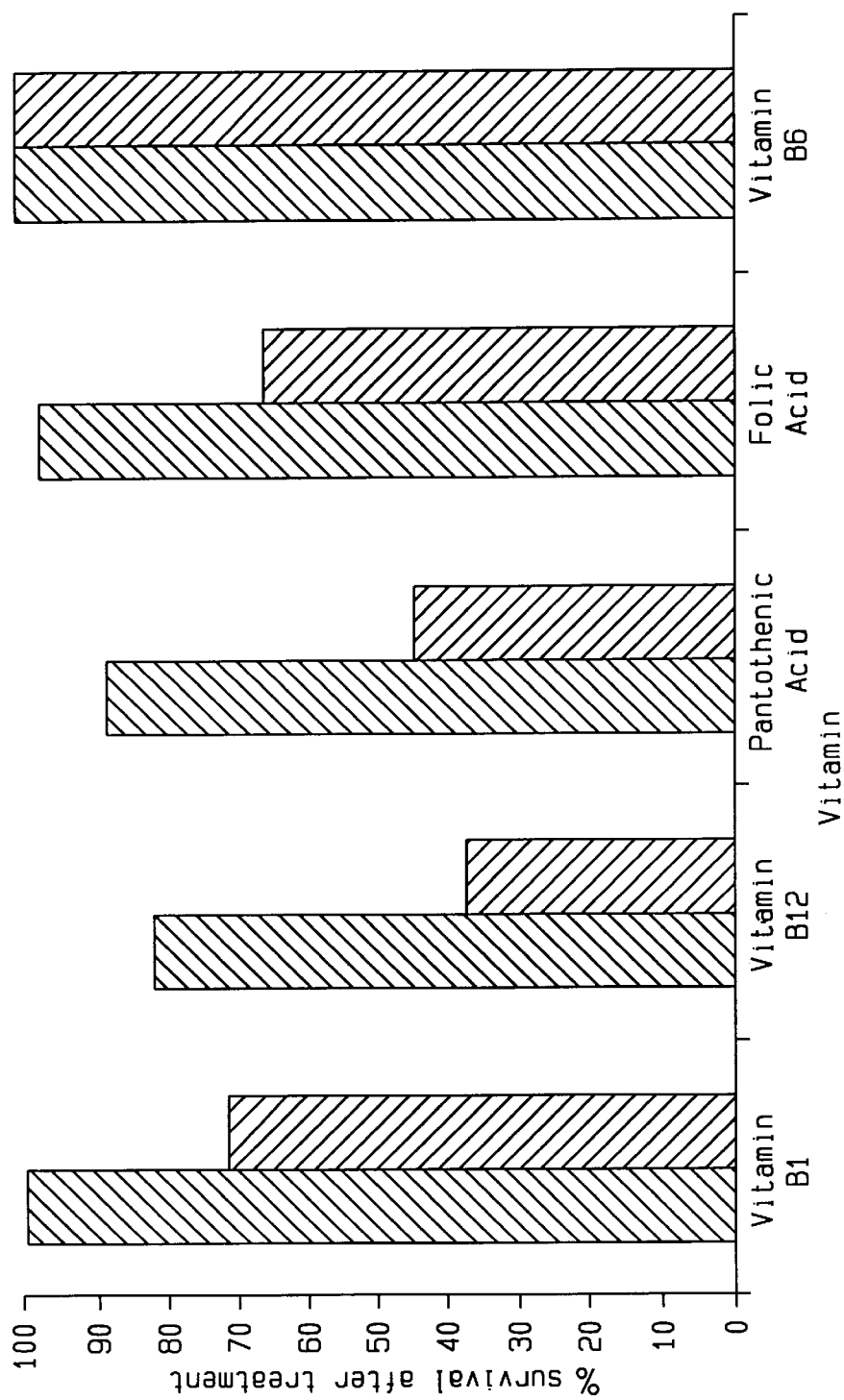
FIG. 3 is a bar graph illustrating core material retention during encapsulation of high pressure or heat denaturation of proteins.

A solution of 350 parts of water, 100 parts of whey protein (same as Example 2) and 50 parts of micronutrient vitamin premix (same as Example 2) was placed in a plastic pouch and denatured under high pressure (60,000 psi for 20 min at room temperature, and pH 7. The resulting gel matrix was ground and vacuum dried. The resulting microcapsules were analyzed for vitamin content and FIG. 3 shows that the retention of all the vitamins was very high.

Comparative Example B

A similar procedure to that described in Example 3 was followed except that, instead of the high pressure treatment in a plastic pouch, the denaturing was carried out by heating the composition at 95° C. for 15 minutes. FIG. 3 shows that the retention of four of the five vitamins was significantly less when compared with the high pressure treated Sample of Example 3.

What is claimed is:

1. A process for encapsulating a core material which comprises mixing the core material with an aqueous polymer medium comprising a natural food polymer, treating the formed mixture at a pressure of from about 15,000 to 200,000 psi for a time of at least 30 seconds at a temperature of from about 0° to 100° C. to form a gel matrix comprising the core material encapsulated within the natural food polymer, and then drying the formed gel matrix.

2. A process according to claim 1 which comprises, before the pressure treatment, mixing the formed mixture with melted fat to form a water in oil emulsion containing droplets, cooling the emulsion to solidify the fat phase, then pressure treating the emulsion to transform the droplets into gel particles, separating the gel particles from the fat phase and washing the separated gel particles.

3. A process according to claim 1 wherein the core material is a flavor, color, vitamin, mineral, spice, oil or pharmaceutical.

4. A process according to claim 1 wherein the core material is heat sensitive or chemically sensitive.

5. A process according to claim 1 wherein the natural food polymer is a whey protein, casein, gelatin, human serum albumin, egg white, soy isolate, pectin or carboxymethyl cellulose.

6. A process according to claim 1 wherein the natural food polymer is water-insoluble after the high pressure treatment.

7. A process according to claim 1 wherein the core material is mixed with the aqueous polymer medium by dissolving, emulsifying or dispersing it into an aqueous solution or dispersion or slurry of the polymer.

8. A process according to claim 1 wherein the formed mixture is treated at a temperature of from about 15° to 60° C.

9. A process according to claim 1 wherein the formed mixture is treated in a hydrostatic press.

10. A process according to claim 1 wherein the formed mixture is sealed in a flexible bag made of rubber or plastics material before being treated.

11. A process according to claim 1 wherein the formed mixture is treated for a duration of about 1 to 60 minutes.

12. A process according to claim 1 wherein the amount of core material in the mixture with the aqueous polymer medium is from about 0.5 to 15% by weight based on the total weight of the mixture and the amount of the polymer in the aqueous polymer medium is from about 1 to 50% by weight based on the total weight of the aqueous polymer medium.

13. A process according to claim 1 which comprises forming an emulsion of the formed mixture; pressure treating the emulsion to form gel particles and obtaining the gel particles for use as the gel matrix.

14. A process according to claim 1 wherein, after the formed mixture is treated, the gel matrix is dried and ground to form capsules having the desired particle size.

15. A process according to claim 14 wherein the gel matrix is first dried then ground.

16. A process according to claim 14 wherein the gel matrix is first ground and then dried.

17. A process for encapsulating a core material which comprises mixing the core material with an aqueous medium comprising a natural polymer, treating the formed mixture at a pressure of from about 15,000 to 200,000 psi for a time of at least 30 seconds at a temperature of from about 15° to 60° C. to form a gel matrix comprising the core material encapsulated within the natural polymer, and then drying the formed gel matrix to form spherical particles having a particle size of from 1 to 3 microns.

18. The process according to claim 1, wherein the pressure is at least about 40,000 psi.

19. The process according to claim 1, wherein the pressure is at least about 60,000 psi.

20. The process according to claim 17, wherein the pressure is at least about 40,000 psi.

* * * * *

UNITED STATES PATENT AND TRADEMARK OFFICE
CERTIFICATE OF CORRECTION

PATENT NO.   : 6,048,562
DATED        : April 11, 2000
INVENTOR(S)  : Zenon Loannis Mandralis et al.

Page 1 of 1

It is certified that error appears in the above-identified patent and that said Letters Patent is hereby corrected as shown below:

<u>Title page,</u>
After "[22] Filed: June 28, 1996, please add the following:
   -- Related U.S. Application Data
  [60] Provisional application No. 60/000,672, June 29, 1995. --

Signed and Sealed this

Eleventh Day of September, 2001

Attest:

*Nicholas P. Godici*

NICHOLAS P. GODICI
*Attesting Officer*     *Acting Director of the United States Patent and Trademark Office*